US009289765B2

(12) United States Patent  (10) Patent No.: US 9,289,765 B2
Kim et al.  (45) Date of Patent: Mar. 22, 2016

(54) MICRO-FLUIDIC DEVICE AND SAMPLE TESTING APPARATUS USING THE SAME

(75) Inventors: Do Gyoon Kim, Yongin-si (KR); Han Sang Kim, Osan-si (KR); Yang Ui Lee, Seoul (KR); Yoon Kyoung Cho, Suwon-si (KR); Na Hui Kim, Suwon-si (KR); Sang Bum Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 47 days.

(21) Appl. No.: 13/170,927

(22) Filed: Jun. 28, 2011

(65) Prior Publication Data

US 2011/0256026 A1    Oct. 20, 2011

Related U.S. Application Data

(63) Continuation-in-part of application No. 12/544,636, filed on Aug. 20, 2009.

(30) Foreign Application Priority Data

Sep. 23, 2008   (KR) .................. 10-2008-0093372
Sep. 3, 2010    (KR) .................. 10-2010-0086520

(51) Int. Cl.
    *B01L 3/00*    (2006.01)
    *G01N 21/00*   (2006.01)
    (Continued)

(52) U.S. Cl.
    CPC ......... *B01L 3/502753* (2013.01); *B01L 3/5027* (2013.01); *B01L 3/50273* (2013.01); *B01L 2200/0605* (2013.01); *B01L 2200/0621* (2013.01); *B01L 2200/10* (2013.01);
    (Continued)

(58) Field of Classification Search
    CPC ............... B01L 2400/0409; B01L 2300/0864; B01L 2300/0867; B01L 2200/0605; B01L 2200/0621; B01L 3/5027; B01L 2400/0677; B01L 2200/10; B01L 2200/16; B01L 3/502753; B01L 2300/0861; G01N 2035/04
    USPC .......................... 422/68.1, 72, 502–507, 537
    See application file for complete search history.

(56) References Cited

U.S. PATENT DOCUMENTS

| 4,663,296 A | 5/1987 | Revillet et al. |
| 5,518,930 A * | 5/1996 | Burd .............................. 436/45 |

(Continued)

FOREIGN PATENT DOCUMENTS

FR   2 575 293 A1   6/1986

OTHER PUBLICATIONS

Extended European Search Report issued Jan. 26, 2010 in counterpart European Application No. 09168441.5.

*Primary Examiner* — Lyle Alexander
*Assistant Examiner* — Jennifer Wecker
(74) *Attorney, Agent, or Firm* — Sughrue Mion, PLLC

(57) ABSTRACT

A microfluidic device having a delay structure and a sample testing apparatus including the microfluidic device are provided. The microfluidic device includes: a reaction chamber which contains a reagent capable of reacting with a sample; a distribution channel through which the sample is provided to the reaction chamber; an inlet channel through which the at least one reaction chamber is connected with the distribution channel; and a delay structure which is located between the at least one reaction chamber and the distribution channel, and delays movement of contents of the reaction chamber to the distribution channel.

19 Claims, 12 Drawing Sheets

(51) Int. Cl.
  *G01N 21/07* (2006.01)
  *G01N 35/00* (2006.01)
  *B01J 19/00* (2006.01)
  *G01N 1/00* (2006.01)
  *G01N 35/04* (2006.01)
  *G01N 33/543* (2006.01)

(52) U.S. Cl.
  CPC ...... *B01L2200/16* (2013.01); *B01L 2300/0806* (2013.01); *B01L 2300/087* (2013.01); *B01L 2300/0861* (2013.01); *B01L 2300/0864* (2013.01); *B01L 2400/0409* (2013.01); *B01L 2400/0677* (2013.01); *G01N 33/54386* (2013.01); *G01N 2035/0449* (2013.01)

(56) References Cited

U.S. PATENT DOCUMENTS

| | | | |
|---|---|---|---|
| 5,591,643 A | 1/1997 | Schembri | |
| 5,693,233 A | 12/1997 | Schembri | |
| 6,235,531 B1 | 5/2001 | Kopf-Sill et al. | |
| 6,302,134 B1 * | 10/2001 | Kellogg et al. | 137/74 |
| 6,326,211 B1 * | 12/2001 | Anderson et al. | 436/177 |
| 7,476,361 B2 * | 1/2009 | Kellogg et al. | 422/72 |
| 2002/0106786 A1 * | 8/2002 | Carvalho et al. | 435/287.3 |
| 2003/0044322 A1 | 3/2003 | Andersson et al. | |
| 2003/0207457 A1 | 11/2003 | Kopf-Sill et al. | |
| 2005/0145497 A1 * | 7/2005 | Gilbert et al. | 204/600 |
| 2005/0249641 A1 * | 11/2005 | Blankenstein et al. | 422/102 |
| 2005/0250199 A1 * | 11/2005 | Anderson et al. | 435/287.2 |
| 2006/0002817 A1 * | 1/2006 | Bohm et al. | 422/57 |
| 2006/0216195 A1 * | 9/2006 | Blankenstein et al. | 422/57 |
| 2009/0053108 A1 * | 2/2009 | Cho et al. | 422/72 |
| 2009/0227041 A1 * | 9/2009 | Wang et al. | 436/180 |
| 2010/0307595 A1 * | 12/2010 | Mark et al. | 137/1 |
| 2012/0121481 A1 * | 5/2012 | Romanowsky et al. | 422/502 |

* cited by examiner

MICRO-FLUIDIC DEVICE AND SAMPLE TESTING APPARATUS USING THE SAME

CROSS-REFERENCE TO RELATED APPLICATIONS

This application is a Continuation-in-Part of U.S. application Ser. No. 12/544,636, filed Aug. 20, 2009, which claims priority from Korean Patent Application No. 10-2008-0093372, filed on Sep. 23, 2008 in the Korean Intellectual Property Office, the disclosures of which are incorporated herein by reference in their entirety. This application also claims priority from Korean Patent Application No. 10-2010-086520, filed Sep. 3, 2010 in the Korean Intellectual Property Office, the disclosure of which is incorporated herein by reference in its entirety.

BACKGROUND

1. Field

Apparatuses and methods consistent with embodiments relate generally to a microfluidic device and a sample testing apparatus using the same and, more particularly, to a microfluidic device having multiple reaction chambers to contain a sample in order to reduce cross-contamination between the chambers, and a sample testing apparatus including the same.

2. Description of the Related Art

A variety of methods for analyzing samples have been developed in various applied fields such as environmental monitoring, food tests, and medical diagnosis. Existing test methods require numerous manual operations and various apparatuses. To perform a test according to a predetermined protocol, an experienced tester needs to manually perform a variety of steps such as reagent loading, mixing, separation and movement, reactions, and centrifuges, several times. Therefore, errors may be easily generated when obtaining results of the test.

Accordingly, an experienced clinical pathologist is needed to quickly perform a test. However, even an experienced clinical pathologist has lots of difficulties in simultaneously performing various tests. For example, in the diagnosis of an urgent case, a quick test result is very important for performing quick emergency treatment. Thus, there is a demand for an apparatus capable of quickly and accurately performing various pathological tests needed according to various situations.

A large and expensive automated apparatus is used for a related art pathological test and a relatively large amount of a test material such as blood is required. Accordingly, a test result may be issued from as long as two days to two weeks after the test material is obtained from a patient.

To address this problem, a compact and automated apparatus has been developed which may quickly analyze a test material(s) obtained from one or more patients if necessary. For example, when blood is loaded in a disk type microfluidic device and the disk type microfluidic device is rotated, serum is separated from the blood due to a centrifugal force. The separated serum is mixed with a predetermined amount of dilution buffer and moved to a plurality of reaction chambers in the disk type microfluidic device. Different reagents are previously loaded in the reaction chambers for different blood test items so that the different reagents react to the serum to present a predetermined color. Blood analysis may be performed by detecting a change in the color.

A device referred to as a "lab-on-a-chip" has a microfluidic structure mounted on a substrate in a chip form, such that some experiments involving biological or chemical reactions can be conducted on a small chip. The lab-on-a-chip is capable of executing several experimental processes and/or operations on the structure.

In order to move a fluid within the microfluidic structure, a driving pressure is generally required. The driving pressure may be a capillary pressure or pressure generated using an additional pump. In recent years, a disc-type microfluidic device, which is referred to as a "lab CD," "lab-on-a-disc" or a digital bio disc (DBD), has been proposed. The disc-type microfluidic device has a microfluidic structure mounted on a disc-type body and uses centrifugal force to move a fluid in order to execute a series of tasks.

In general, the disc-type microfluidic device includes a chamber containing a fluid, a channel through which the fluid flows and a valve for controlling fluid flow, and may be fabricated by combining these components in different ways.

The disc-type microfluidic device may function as a sample testing apparatus to test a sample such as blood. Here, the disc-type microfluidic device may include a plurality of reaction chambers each containing a reagent to react with the sample. The sample inflow into the reaction chamber may react with the reagent contained in the reaction chamber and, by detecting the results of the reaction, a test result of the sample may be obtained.

However, during testing of the sample, contents in any one of the reaction chambers may flow into at least one other chamber adjacent to a first chamber (that is, the former), thus mixing with contents of the other chamber. This is referred to as "cross-contamination" and, as a result, reaction results of the reaction chamber may be unreliable, in turn reducing the reliability of the sample testing apparatus.

In order to reduce such cross-contamination, it is possible to increase a distance between each of the multiple reaction chambers and a provide a sample distribution channel to connect these chambers with one another. However, this is problematic in that it increases the overall size of the disc-type microfluidic device.

SUMMARY

Exemplary embodiments provide a microfluidic device with reduced cross-contamination between at least two reaction chambers of the device and a sample testing apparatus including the microfluidic device.

According to an aspect of an exemplary embodiment, there is provided a microfluidic device including: at least one reaction chamber containing a reagent capable of reacting with a sample; a distribution channel through which the sample is fed into the reaction chamber; an inlet channel for connecting the at least one reaction chamber with the distribution channel; and a delay structure located between the at least one reaction chamber and the distribution channel in order to delay movement of a contents of the at least one reaction chamber toward the distribution channel.

The contents may include the reagent contained in the at least one reaction chamber or a product obtained by reaction of the reagent with the sample.

The delay structure may include a chamber having an inlet and an outlet connected with the inlet channel, respectively.

The delay structure may be formed on the inlet channel.

A cross-sectional area of the delay structure, through which a sample flows, may be at least double a cross-sectional area of the inlet channel.

The inlet channel may be branched from the distribution channel.

A cross-sectional area of the inlet channel may be equal to or smaller than the cross-sectional area of the distribution channel.

When the sample flows through the inlet channel, a resistance to the sample may be substantially equal to or greater than a resistance to the same sample when flowing through the distribution channel.

A valve mounted on an inlet of the distribution channel may be further included.

The opening valve may include a phase transition valve actuated in a non-contact manner by an external energy source.

The sample may be a fluid-type sample.

According to an aspect of another exemplary embodiment, there is provided a microfluidic device including: a sample chamber containing a sample; a distribution channel connected with the sample chamber, through which the sample flows; multiple reaction chambers containing at least one reagent that is capable of reacting with the sample; multiple inlet channels for connecting the reaction chambers with the distribution channel, respectively; and at least one delay structure located between the individual reaction chambers and the distribution channel in order to delay flow of a contents of the reaction chambers into the distribution channel.

The delay structure may be aligned in plural between the distribution channel and the multiple reaction chambers, respectively.

The delay structure may be formed at the inlet channel.

A cross-sectional area of the delay structure, through which a fluid flows, may be at least double a cross-sectional area of the inlet channel.

The distribution channel may have a constant cross-sectional area over the entirety of the distribution channel.

A cross-sectional area of the inlet channel may be substantially equal to or smaller than the cross-sectional area of the distribution channel.

A bottom surface of the distribution channel may be positioned below a bottom surface of the inlet channel.

According to an aspect of another exemplary embodiment, there is provided a centrifugal microfluidic device including: a rotational platform; at least one reaction chamber located on the platform, and which contains a reagent capable of reacting with a sample; a distribution channel through which the sample flows to the at least one reaction chamber; an inlet channel for connecting the at least one reaction chamber with the distribution channel; and at least one delay structure located between the reaction chamber and the distribution channel to delay transfer of a contents of the at least one reaction chamber to the distribution channel.

The distribution channel may be connected with an outlet of the sample chamber and have a first section extending outward in a radial direction of the platform and a second section extending from the first section in a circumferential (rotational) direction of the platform.

The inlet channel may have a cross-sectional area equal to or smaller than that of the second section.

A bottom surface of the second section may be positioned at a level lower than a bottom surface of the inlet channel, so that the inlet channel is connected with the second section by a stepped interval.

According to an aspect of another exemplary embodiment, there is provided a centrifugal microfluidic system including: a microfluidic device including multiple chambers containing a fluid, at least one channel through which the multiple chambers are interconnected and through which the fluid flows, and at least one valve to open and close the at least one channel; a rotational driving device supporting and controllably rotating the microfluidic device; and a valve opening device to open the valve, wherein the microfluidic device has at least one reaction chamber in which a reaction occurs, an inlet channel having an inlet through which the fluid is fed from the at least one channel and an outlet through which the fluid is fed from the inlet channel into the at least one reaction chamber; and a delay chamber located between the inlet and the outlet to delay movement of a contents of the reaction chamber to the inlet.

The centrifugal microfluidic system may further include an optical detection unit in order to optically detect results of a reaction in the at least one reaction chamber.

BRIEF DESCRIPTION OF THE DRAWINGS

The above and/or other aspects will become apparent and more readily appreciated from the following description of the exemplary embodiments, taken in conjunction with the accompanying drawings of which.

DETAILED DESCRIPTION OF EXEMPLARY EMBODIMENTS

Figure 1:
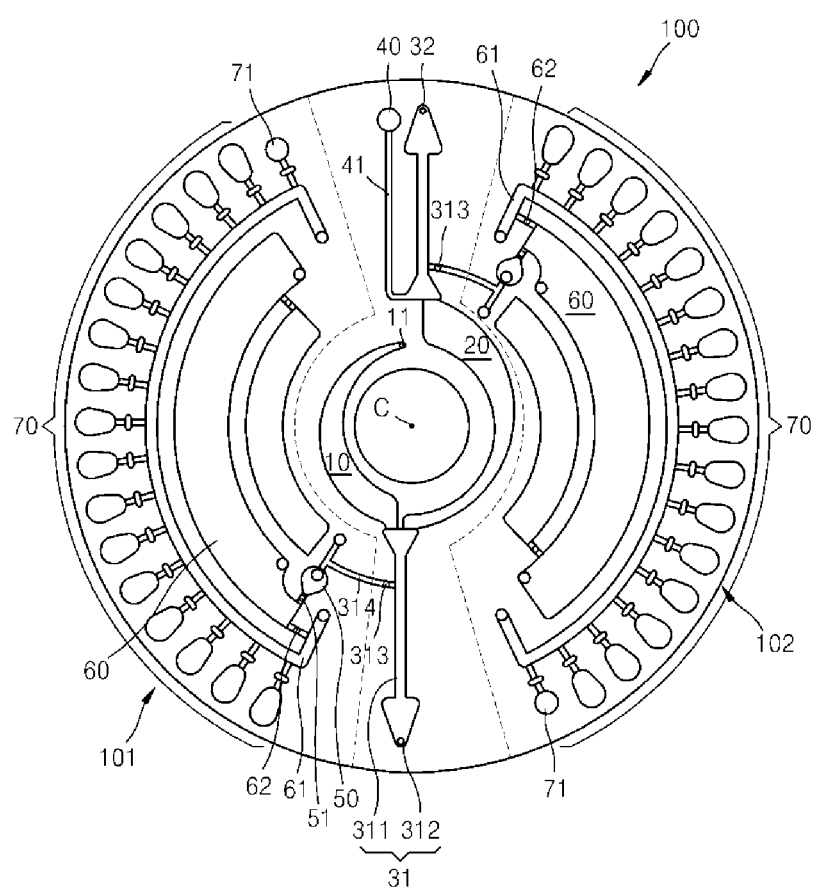
FIG. 1 is a plan view of a microfluidic device, according to an exemplary embodiment.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

FIG. 1 is a plan view of a microfluidic device, according to an exemplary embodiment. Referring to FIG. 1, the microfluidic device according to the present exemplary embodiment includes a platform 100 that is rotatable and has the shape of, for example, a disk, and microfluidic structures providing a space for accommodating a fluid and a path for flowing the fluid, in the platform 100. The platform 100 may be rotated around a center of rotation C. That is, in the structures arranged in the platform 100, a sample may be moved and mixed due to a centrifugal force generated by the rotation of the platform 100.

Figure 2:
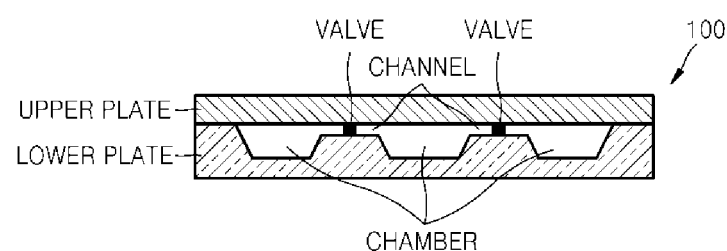
FIG. 2 is a cross-sectional view of a microfluidic device having a double-plated structure, according to an exemplary embodiment.
Figure 3:
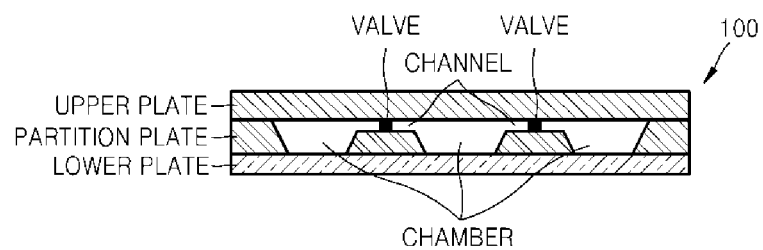
FIG. 3 is a cross-sectional view of a microfluidic device having a three-plate structure, according to an exemplary embodiment.

The platform 100 may be formed of a plastic material such as acryl or polydimethylsiloxane (PDMS) which is easily molded and has a surface that is biologically inactive. However, the platform 100 may be formed of other materials having chemical and biological stability, optical transparency, and mechanical processibility. The platform 100 may be formed of a multi-layered structure. An intaglio structure corresponding to a chamber or a channel is formed in a surface where plates contact each other and combined to provide space and paths in the platform 100. The plates may be combined using a method such as adhesion using an adhesive or double-sided adhesive tape, ultrasonic wave welding, or laser welding. For example, as illustrated in FIG. 2, the platform 100 may have a double-plated structure including a lower plate and an upper plate. Also, according to another exemplary embodiment as illustrated in FIG. 3, the platform 100 may have a partition plate for defining a space for accommodating a fluid and a path for flowing the fluid provided between the lower plate and the upper plate. The platform 100 may have a variety of shapes in addition to the above shapes.

In the microfluidic structures arranged in the platform 100, a position radially closer to the center of rotation C of the platform 100 is referred to as the inner side while a position radially far from the center of rotation C of the platform 100 is referred to as the outer side. A sample chamber 10 for accommodating a sample is of the closest microfluidic structure to the center of rotation C. A loading hole 11 for loading a sample may be provided in the sample chamber 10. First and second sample distribution units 31 and 32 receive the sample from the sample chamber 10 and supply the sample to first and second analysis units 101 and 102. The first and second sample distribution units 31 and 32 may have, for example, a predetermined volume for metering a fixed quantity of a sample needed for a test. Since the centrifugal force generated by the rotation of the platform 100 is used to move the sample from the sample chamber 10 to the first and second sample distribution units 31 and 32, the first and second sample distribution units 31 and 32 are positioned at the outer side of the sample chamber 10. The first and second sample distribution units 31 and 32 may be arranged in a circumferential direction with respect to each other.

Figure 4:
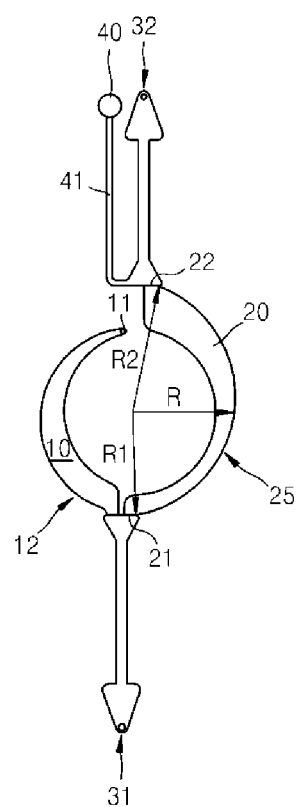
FIG. 4 illustrates in detail a sample transfer unit and a sample distribution unit of FIG. 1, according to an exemplary embodiment.

At least one of the first and second sample distribution units 31 and 32 may have a structure to centrifugally separate a sample. For example, the first sample distribution unit 31 may work as a centrifuge for separating supernatant and sediment from a sample, for example, blood, using the rotation of the platform 100. The first sample distribution unit 31 for centrifugation may have a variety of shapes, and an example thereof is illustrated in FIGS. 1 and 4. The first sample distribution unit 31 may include a supernatant collection unit 311 having a channel shape extending outwardly in a radial direction and a sediment collection unit 312 located at an end portion of the supernatant collection unit 311 to provide a space for collection of a sediment having a relatively large specific gravity. According to the above structure, a test item that is required to be centrifuged and a test item that is not required to be centrifuged may be tested using a single microfluidic device.

The first sample distribution unit 31 is directly connected to the sample chamber 10 to receive a sample. The second sample distribution unit 32 is connected to the first sample distribution unit 31 by a sample transfer unit 20. Accordingly, the sample is supplied from the sample chamber 10 to the first sample distribution unit 31 to fill the first sample distribution unit 31, and then is supplied by the sample transfer unit 20 to fill the second sample distribution unit 32.

Referring to FIG. 4, the sample transfer unit 20 forms a path for moving a sample and includes a first connection unit 21 connected to the first sample distribution unit 31 and a second connection unit 22 connected to the second sample distribution unit 32. The first and second connection units 21 and 22 may be provided at an outer wall 25 of the sample transfer unit 20. The radius R2 from the center of rotation C to the second connection unit 22 is greater than the radius R1 from the center of rotation C to the first connection unit 21, that is, R1<R2 in FIG. 4. Also, the radius of curvature R of the outer wall 25 between the first and second connection units 21 and 22 is not less than R1 and gradually increases from the first connection unit 21 to the second connection unit 22. According to the above structure, when the microfluidic device rotates, the sample is moved to the first sample distribution unit 31 due to the centrifugal force and fills the first sample distribution unit 31 and then is moved to the sample transfer unit 20. Then, the sample is moved along the outer wall 25 of the sample transfer unit 20 to the second sample distribution unit 32 via the second connection unit 22.

As described above, the plurality of sampling distribution units for receiving samples from a single sample chamber may alleviate inconvenience of loading the sample into each of the plurality of sample distribution units. The microfluidic device according to the present exemplary embodiment may further include an excess sample chamber 40. The excess sample chamber 40 is connected to the second sample distribution unit 32 via a channel 41. The excess sample left after filling the second sample distribution unit 32 is moved to and accommodated in the excess sample chamber 40 via the channel 41.

The first and second analysis units 101 and 102 may be units for testing items requiring different dilution ratios. For example, among the blood test items, ALB (Albumin), ALP (Alakaline Phosphatase), AMY (Amylase), BUN (Urea Nitrogen), Ca++(calcium), CHOL (Total Cholesterol), Cl− (Chloide), CRE (Creatinine), GLU (Glucose), HDL (High-Density Lipoprotein cholesterol), K+(Potassium), LD (Lactate Dehydrogenase), Na+ (Sodium), T-BIL (Total Bilirubin), TP (Total Protein), TRIG (Triglycerides), UA (Uric Acid) require a dilution ratio of serum:dilution buffer of 1:100. Also, ALT (alanine aminotransferase), AST (aspartate aminotransferase), CK (Creatin Kinase), D-BIL (Direct Bilirubin), GGT (Gamma Glutamyl Transferase) require a dilution ratio of serum:dilution buffer=1:20. Thus, the first analysis unit 101 may be a unit for testing the items requiring the dilution ratio of serum:dilution buffer of 1:100 and the second analysis unit 102 may be a unit for testing the items requiring the dilution ratio of serum:dilution buffer of 1:20.

The first and second analysis units 101 and 102 may test items having the same dilution ratio. Also, the first analysis unit 101 is for testing items that require centrifugation and the second analysis unit 102 is for testing items that do not require centrifugation. Since the first and second analysis units 101 and 102 have substantially the same structure, only the structure of the first analysis unit 101 will be discussed below in detail.

A sample distribution channel 314 for distributing a collected supernatant, for example, serum when blood is used as a sample, to a structure in which the next step is performed is arranged at a side of the supernatant collection unit 311. The sample distribution channel 314 is connected to the supernatant collection unit 311 via a valve 313. The position at which the sample distribution channel 314 is connected to the supernatant collection unit 311 may vary according to the amount of the sample to be distributed. That is, the amount of the sample to be distributed is dependent on the volume of a portion of the supernatant collection unit 312 that is close to the center of rotation C with respect to the valve 313. In the strict sense, when a metering chamber 50 is further provided as described later, the amount of the sample to be distributed is dependent on the volume of the metering chamber 50.

The valve 313 may be a microfluidic valve having a variety of shapes. In this regard, the valve 313 may be a capillary valve that is passively opened when a pressure exceeding a predetermined value is applied, or a valve actively operating by receiving external power or energy according to an operating signal. The valve 313 is a so-called normally closely valve that closes the sample distribution channel 314 to block the flow of a fluid before absorbing electromagnetic energy.

The valve 313 may be formed of thermoplastic resin such as COC (cyclic olefin copolymer), PMMA (polymethylmethacrylate), PC (polycarbonate), PS(polystyrene), POM (polyoxymethylene), PFA (perfluoralkoxy), PVC (polyvinylchloride), PP (polypropylene), PET (polyethylene terephthalate), PEEK (polyetheretherketone), PA (polyamide), PSU (polysulfone), or PVDF (polyvinylidene fluoride).

Also, the valve 313 may be formed of a phase transition material that is in a solid state at room temperature. The phase transition material is loaded into the sample distribution channel 314 in a molten state and then solidified to block the sample distribution channel 314. The phase transition material may be wax. When heated, the wax is melted and changes to a liquid state so that the volume of the phase transition material expands. The wax may be paraffin wax, microcrystalline wax, synthetic wax, or natural wax. The phase transition material may be gel or thermoplastic resin. The gel may be polyacrylamide, polyacrylates, polymethacrylates, or polyvinylamides.

A plurality of micro heating particles that generate heat by absorbing electromagnetic wave energy may be distributed in the phase transition material. The micro heating particles may each have a diameter of about 1 nm to 100 mm so as to freely pass through the sample distribution channel 314 that is may be about 0.1 mm deep and 1 mm wide. The micro heating particles characteristically generate heat by being quickly heated when subjected to electromagnetic wave energy supplied by, for example, a laser beam. As another characteristic, the micro heating particles are uniformly distributed throughout the phase transition material. To ensure the above characteristic, the micro heating particles may have a core having a metal ingredient and a hydrophobic surface structure. For example, the micro heating particles may have a Fe core and a molecule structure having a plurality of surfactants combined with Fe and encompassing the Fe. The micro heating particles may be kept in a state of being distributed in carrier oil. The carrier oil may be hydrophobic so that the micro heating particles having a hydrophobic surface structure may be uniformly distributed. The carrier oil in which the micro heating particles are distributed is poured to be mixed with the molten phase transition material. The mixture is loaded into the sample distribution channel 314 and solidified so that the sample distribution channel 314 may be blocked.

The micro heating particles are not limited to the above-described polymer particles and quantum dots or magnetic beads may also be employed. Also, the micro heating particles may be micro-metal oxides such as $Al_2O_3$, $TiO_2$, $Ta_2O_3$, $Fe_2O_3$, $Fe_3O_4$, or, $HfO_2$. The valve 313 does not necessarily include the micro heating particles and may be formed of only the phase transition material without the micro heating particles. At least a part of the platform 100 is transparent so that electromagnetic waves emitted from outside the platform 100 can be irradiated on the sample distribution channel 314.

The sample distribution channel 314 is connected to the metering chamber 50 that accommodates the supernatant separated from the sample. The metering chamber 50 is connected to a dilution chamber 60 via a valve 51. The valve 51 may be a microfluidic valve of the same type as the above-described valve 313.

The dilution chamber 60 is for providing a sample dilution buffer in which supernatant and a dilution buffer are mixed in a predetermined ratio. A predetermined amount of a dilution buffer is accommodated in the dilution chamber 60 considering the dilution ratio between the supernatant and the dilution buffer needed for the test. The metering chamber 50 may be designed to have a volume capable of accommodating the amount of sample determined considering the dilution ratio. As long as the valve 51 is kept closed, the sample of an amount exceeding the volume of the metering chamber 50 may not be input to the metering chamber 50. Accordingly, only a fixed amount of the supernatant may be supplied to the dilution chamber 60. As described above, by precisely designing the position at which the sample distribution channel 314 is connected to the supernatant collection unit 311, the sample distribution channel 314 may be directly connected to the dilution chamber 60.

A plurality of reaction chambers 70 are arranged circumferentially outside the dilution chamber 60. The reaction chambers 70 are connected to the dilution chamber 60 via a distribution channel 61. The distribution of a sample dilution buffer via the distribution channel 61 may be controlled by a valve 62. The valve 62 may be a microfluidic valve of the same type of the above-described valve 313.

The reaction chambers 70 may accommodate reagents generating different types of reactions with a sample dilution buffer. The reagents may be loaded into the reaction chambers 70 before an upper plate and a lower plate are combined to form the platform 100 during the manufacture of the microfluidic device. Also, the reaction chambers 70 may be either closed reaction chambers or reaction chambers having a vent and a loading hole. The reagents may be in a liquid state or a lyophilized solid state.

For example, reagents in a liquid state may be loaded into the reaction chambers 70 before the upper and lower plates forming the platform 100 are combined with each other during the manufacture of the microfluidic device and the reagents may be simultaneously lyophilized according to a lyophilisation program. Then, the upper and lower plates are combined to accommodate the lyophilized reagents. Also, cartridges accommodating the lyophilized reagents may be inserted into the reaction chambers 70. The lyophilized reagent may be obtained by adding a filler and a surfactant to a liquid reagent and lyophilizing the same. The filler helps the lyophilized reagent to have a porous structure and facilitates later the solution of a diluted buffer obtained by mixing the reagent and the diluted buffer input to the reaction chambers 70.

The filler may be selected from a group consisting of BSA (bovine serum albumin), PEG (polyethylene glycol), dextran, mannitol, polyalcohol, myo-inositol, citric acid, EDTA2Na (ethylene diamine tetra acetic acid disodium salt), and BRIJ-35 (polyoxyethylene glycol dodecyl ether). Of the above fillers, one or more fillers may be selected and added according to the type of the reagent. For example, the surfactant may be selected from a group consisting of polyoxyethylene, lauryl ether, octoxynol, polyethylene alkyl alcohol, nonylphenol polyethylene glycol ether; ethylene oxid, ethoxylated tridecyl alcohol, polyoxyethylene nonylphenyl ether phosphate sodium salt, and sodium dodecyl sulfate. Of the above surfactants, one or more surfactants may be selected and added according to the type of the reagent.

A detection chamber 71 is provided to determine whether a sampling diluted buffer is loaded into all of the reaction chambers 70. The detection chamber 71 does not accommodate the reagent and is provided at an end portion of the distribution channel 61. The sampling diluted buffer first fills the reaction chamber 70 that is closest to the dilution chamber 60 and the detection chamber 71 last. Thus, by checking whether the detection chamber 71 is filled with the sampling diluted buffer, it can be determined whether all of the reaction chambers 70 are filed with the sampling diluted buffer. Although not shown, an air vent for exhausting internal air may also be provided in the microfluidic device.

Figure 5:
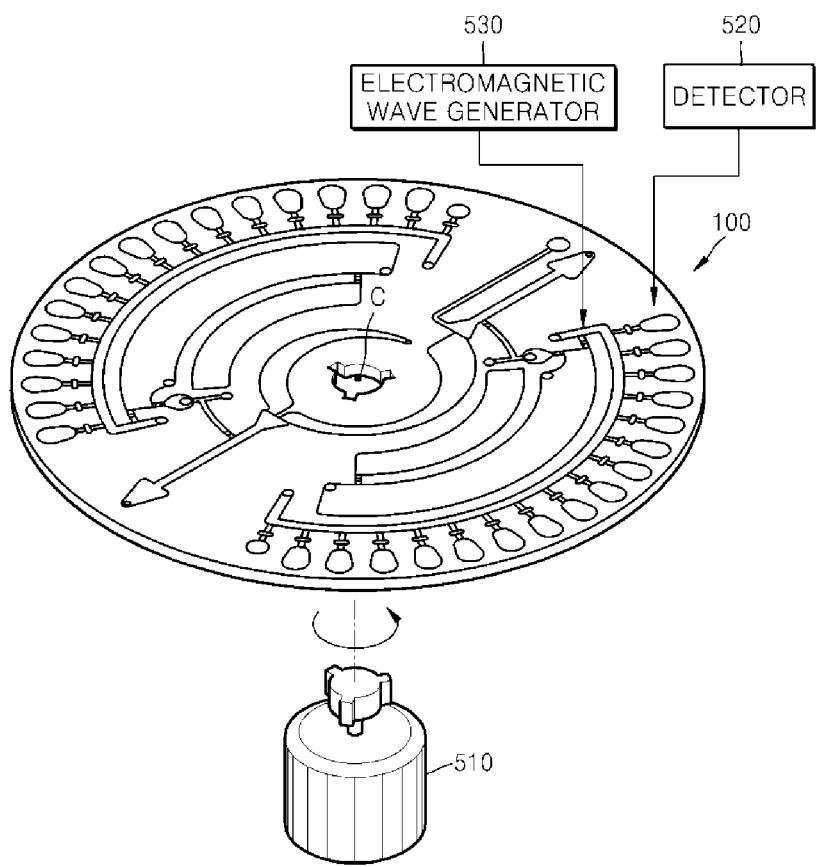
FIG. 5 is a perspective view of an analyzer using the microfluidic device of FIG. 1, according to an exemplary embodiment.

FIG. 5 is a perspective view of an analyzer using the microfluidic device of FIG. 1. Referring to FIG. 5, the analyzer includes a rotation drive unit 510 rotating the microfluidic device to move a sample to a predetermined position in the microfluidic device. Also, the rotation drive unit 510 rotates the microfluidic device to centrifuge the sample and move a separated supernatant to a predetermined position in the microfluidic device. Also, the rotation drive unit 510 stops the microfluidic device at a predetermined position so that one of the reaction chambers 70 faces a detector 520 and the valves face an electromagnetic wave generator 530. The rotation drive unit 510 may have a motor drive unit (not shown) capable of controlling an angular position of the microfluidic device. The motor drive unit may use a step motor or a DC motor. The detector 520 detects, for example, a fluorescence/illumination characteristic, and/or an optical characteristic such as light absorption, of a material to be detected. The electromagnetic wave generator 530 operates the valves by, for example, emitting a laser beam. The electromagnetic wave generator 530 may be moved in a radial direction of the microfluidic device.

In the sample analysis process using the microfluidic device, a sample is initially loaded into the sample chamber 10. A liquid dilution buffer such as a buffer solution or distilled water is loaded into the dilution chamber 60. In doing so, an appropriate amount of a dilution buffer is loaded into the dilution chamber 60 such that a dilution ratio of the sample dilution buffer may be suitable for a test item.

The microfluidic device is installed on the rotation drive unit 510 of the analyzer as illustrated in FIG. 5. The rotation drive unit 510 rotates the microfluidic device at a slow speed. The slow speed signifies a rotation speed suitable for moving the sample from the sample chamber 10 to the first and second sample distribution units 31 and 32. Then, the sample accommodated in the sample chamber 10 is moved to the first sample distribution unit 31 by a centrifugal force to fill the first sample distribution unit 31. When the first sample distribution unit 31 is completely filled with the sample, the sample is input to the sample transfer unit 20 via the first connection unit 21. Due to the centrifugal force, the sample flows along the outer wall 25 of the sample transfer unit 20 to be input to the second sample distribution unit 32 via the second connection unit 22. After completely filling the second sample distribution unit 32, the remaining sample is moved to the excess sample chamber 40 along the channel 41 and accommodated in the excess sample chamber 40.

Next, a sample analysis operation is performed. For instance, when the test item of the second analysis unit 102 does not require centrifugation, the analysis using the second analysis unit 102 may be first performed. The rotation drive unit 510 rotates the microfluidic device so that the valve 313 faces the electromagnetic wave generator 530. When electromagnetic waves are irradiated to the valve 313, the valve material forming the valve 313 is changed to a liquid state due to the energy of the electromagnetic waves, thereby opening the channel 314. The rotation drive unit 510 rotates the microfluidic device at a rotation speed at which a centrifugal separation is not generated. Then, due to the rotation of the microfluidic device, the sample accommodated in the second sample distribution unit 32 flows to the metering chamber 50 along the channel 314 due to the centrifugal force. The rotation drive unit 510 rotates the microfluidic device so that the valve 51 faces the electromagnetic wave generator 530. When electromagnetic waves are irradiated to the valve 51, the valve material forming the valve 51 is changed to a liquid state due to the energy of the electromagnetic waves, and thus the valve 51 is opened so that the sample is input to the dilution chamber 60. The rotation drive unit 510 may shake the microfluidic device to the left and right, several times, to mix the sample and the dilution buffer. Accordingly, a sample dilution buffer in which the sample and the dilution buffer are mixed is formed in the dilution chamber 60. The rotation drive unit 510 rotates the microfluidic device so that the valve 62 faces the electromagnetic wave generator 530. When electromagnetic waves are irradiated to the valve 62, the valve material forming the valve 62 is melted due to the energy of the electromagnetic waves, thereby opening the distribution channel 61. As the microfluidic device rotates, the sample dilution buffer is input to the reaction chambers 70 and the detection chamber 71 via the distribution channel 61 due to the centrifugal force. After the microfluidic device is rotated in order for the detection chamber to face the detector 520, a light absorption value of the detection chamber 71 is measured to determine whether the detection chamber 71 includes the sample dilution buffer. The reagent accommodated in the reaction chambers 70 is mixed with the sample dilution buffer. To mix the reagent and the sample dilution buffer, the rotation drive unit 510 may shake the microfluidic device to the left and right, several times, to mix the sample and the sample dilution buffer. Then, after the microfluidic device is rotated in order for the reaction chambers 70 to face the detector 520, light is irradiated to the mixture of the reagent and the sample dilution buffer so that the fluorescence/illumination characteristic, and/or an optical characteristic such as light absorption, are detected. As a result, it can be determined whether a particular material exists in the mixture and/or how large the amount of the material is.

In an operation of testing an item requiring centrifugation using the first analysis unit 101, the rotation drive unit 510 rotates the microfluidic device at a high speed. The high speed signifies a rotation speed at which the sample is centrifuged. Then, supernatant is concentrated at the supernatant collection unit 311 and a material having a heavy mass is concentrated at the sediment collection unit 312. The rotation drive unit 510 rotates the microfluidic device in order for the valve 313 to face the electromagnetic wave generator 530. When electromagnetic waves are irradiated to the valve 313, the valve material forming the valve 313 is melted due to the energy of the electromagnetic waves, thereby opening the channel 314. As the microfluidic device is rotated, the supernatant is moved to the metering chamber 50 along the channel 314 due to the centrifugal force. The rotation drive unit 510 rotates the microfluidic device in order for the valve 51 to face the electromagnetic wave generator 530. When electromagnetic waves are irradiated to the valve 51, the valve material forming the valve 51 is melted due to the energy of the electromagnetic waves, and thus the sample is input to the dilution chamber 60. The rotation drive unit 510 may shake the microfluidic device to the left and right, several times, to mix the supernatant and the dilution buffer. Accordingly, a sample dilution buffer in which the supernatant and the dilution buffer are mixed is formed in the dilution chamber 60. The rotation drive unit 510 rotates the microfluidic device in order for the valve 62 to face the electromagnetic wave generator 530. When electromagnetic waves are irradiated to the valve 62, the valve material forming the valve 62 is melted due to the energy of the electromagnetic waves, thereby opening the distribution channel 61. As the microfluidic device rotates, the sample dilution buffer is input to the reaction chambers 70 and the detection chamber 71 via the distribution channel 61 due to the centrifugal force. After the microfluidic device is rotated in order for the detection chamber 71 to face the detector 520, a light absorption value of the detection chamber 71 is measured to determine whether the detection chamber 71 includes the sample dilution buffer. The reagent accommodated in the reaction chambers 70 is mixed with the sample dilution buffer. To mix the reagent and the sample dilution buffer, the rotation drive unit 510 may shake the microfluidic device to the left and right, several times, to mix the sample and the sample dilution buffer. Then, after the microfluidic device is rotated in order for reaction chambers 70 to face the detector 520, light is emitted to the mixture of the reagent and the sample dilution buffer so that the fluorescence/illumination characteristic, and/or an optical characteristic such as light absorption, are detected. As a result, it can be determined whether a particular material exists in the mixture and/or how much of the material exists.

In the above-described sample analysis process, the sample required to be centrifuged is analyzed after the sample not required to be centrifuged is analyzed. However, the exemplary embodiments are not limited to the above sample analysis sequence. For example, the sample may be simultaneously distributed from the sample chamber 10 to the first and second sample distribution units 31 and 32. The sample not required to be centrifuged is mixed with the dilution buffer to thus produce a first sample dilution buffer. The sample required to be centrifuged is centrifuged and the obtained supernatant is mixed with the dilution buffer to thus produce a second sample dilution buffer. Then, the first and second sample dilution buffers are moved to the detection chamber of a corresponding analysis unit and mixed with the reagent so that it may be determined whether a particular material exists in the mixture and/or how much of the material exists.

Figure 6:
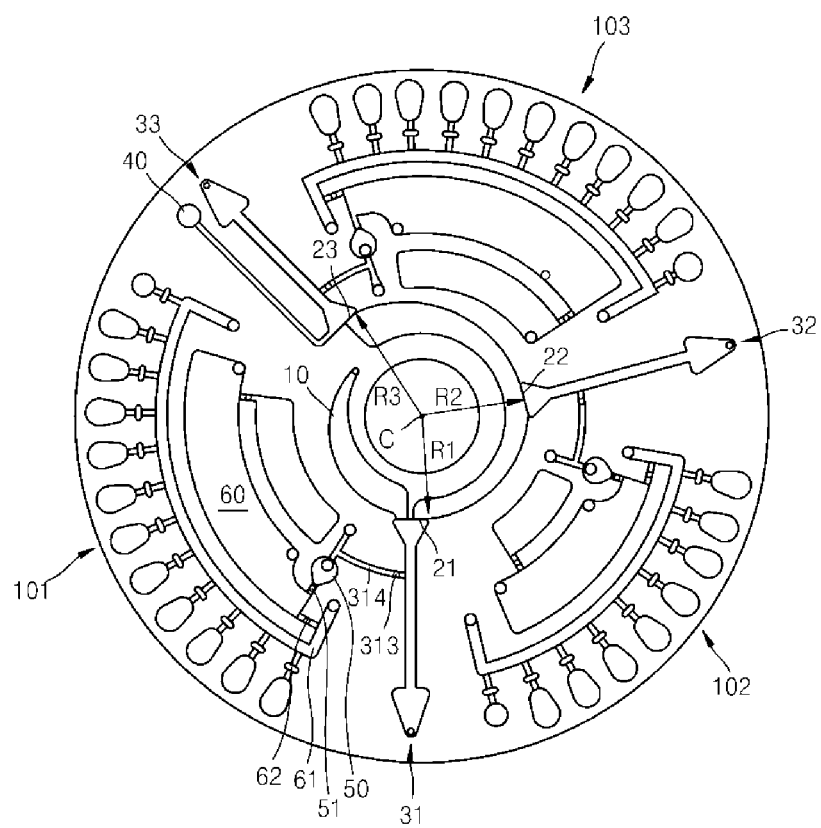
FIG. 6 is a plan view of a microfluidic device, according to another exemplary embodiment.

FIG. 6 is a plan view of a microfluidic device according to another exemplary embodiment. Referring to FIG. 6, the microfluidic device according to the present exemplary embodiment includes the first sample distribution unit 31, the first analysis unit 101, the second sample distribution unit 32, the second analysis unit 102, a third sample distribution unit 33, and a third analysis unit 103. The first, second and third sample distribution units 31, 32 and 33 are arranged in a circumferential direction. The sample transfer unit 20 includes the first connection unit 21 connected to the first sample distribution unit 31, the second connection unit 22 connected to the second sample distribution unit 32, and a third connection unit 23 connected to the third sample distribution unit 33. The radius R2 from the center of rotation C of the microfluidic device to the second connection unit 22 is greater than the radius R1 from the center of rotation C of the microfluidic device to the first connection unit 21. Also, a radius R3 from the center of rotation C of the microfluidic device to the third connection unit 23 that is relatively far from the first connection unit 21 is greater than the radius R2 from the center of rotation C of the microfluidic device to the second connection unit 22 that is relatively close to the first connection unit 21. That is, $R1<R2<R3$. The excess sample chamber 40 is connected to the third sample distribution unit 33 which is connected to the third connection unit 23 of the sample transfer unit 20. The first, second and third analysis units 101, 102 and 103 may test items requiring the same or different dilution ratios. The structure of the third analysis unit 103 may be the same as those of the first analysis unit 101 and the second analysis unit 102.

Figure 7:
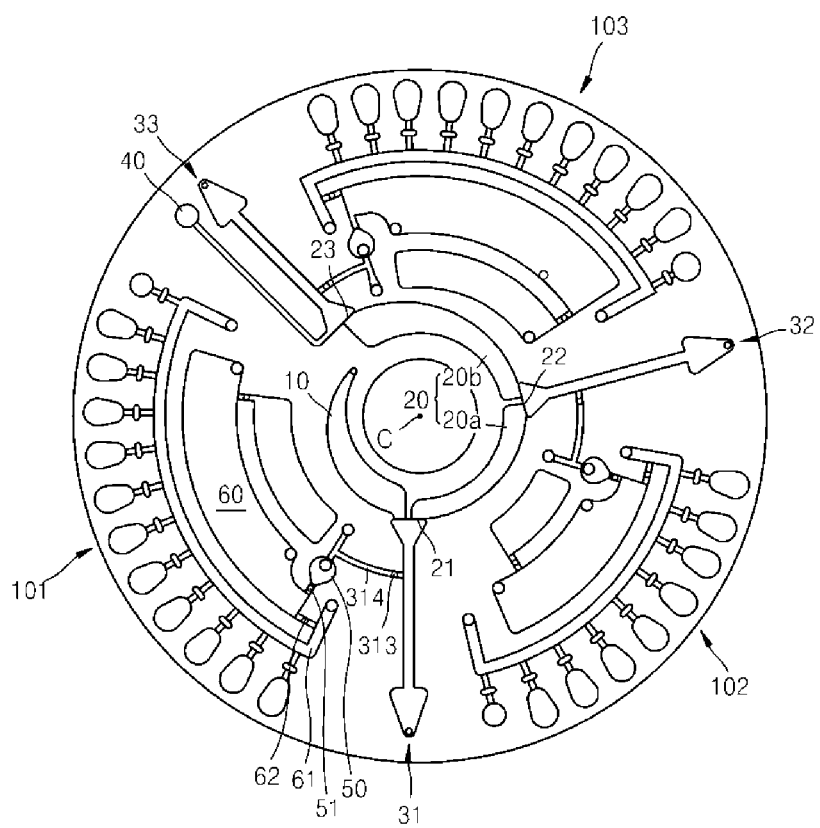
FIG. 7 is a plan view of a microfluidic device, according to another exemplary embodiment.

FIG. 7 is a plan view of a microfluidic device according to another exemplary embodiment. Referring to FIG. 7, the structure of the microfluidic device according to the present exemplary embodiment is the same as that of the microfluidic device of FIG. 6, except that the sample transfer unit 20 is divided into two sub-transfer units 20a and 20b.

Figure 8:
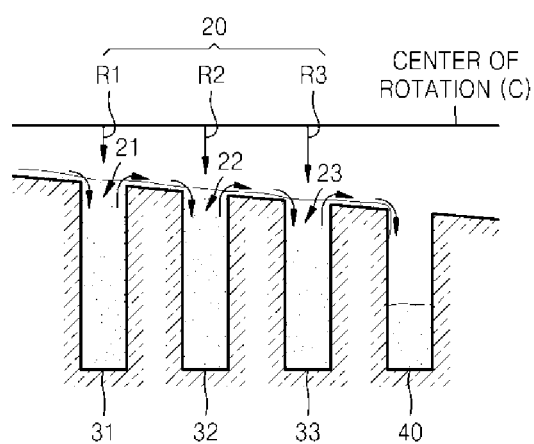
FIG. 8 illustrates the movement of a sample in the microfluidic devices illustrated in FIGS. 6 and 7, according to an exemplary embodiment.

FIG. 8 illustrates the movement of a sample in the microfluidic devices illustrated in FIGS. 6 and 7, according to an exemplary embodiment. Referring to FIG. 8, since the distances from the center of rotation C of the microfluidic device to the first, second and third connection units 21, 22, and 23 are R1, R2 and R3, respectively, wherein $R1<R2<R3$, the sample comes out of the sample chamber 10 and sequentially fills the first, second and third connection units 21, 22, and 23 in this order. The remaining sample is accommodated in the excess sample chamber 40.

As described above, according to the one or more exemplary embodiments, the microfluidic device may be used to analyze a variety of samples obtained from a human body and any living organisms, in addition to blood. Also, although two or three sample distribution units and analysis units are provided in the above-described exemplary embodiments, the exemplary embodiments are not limited thereto, and four or more sample distribution units and analysis units may be provided if necessary.

Figure 9:
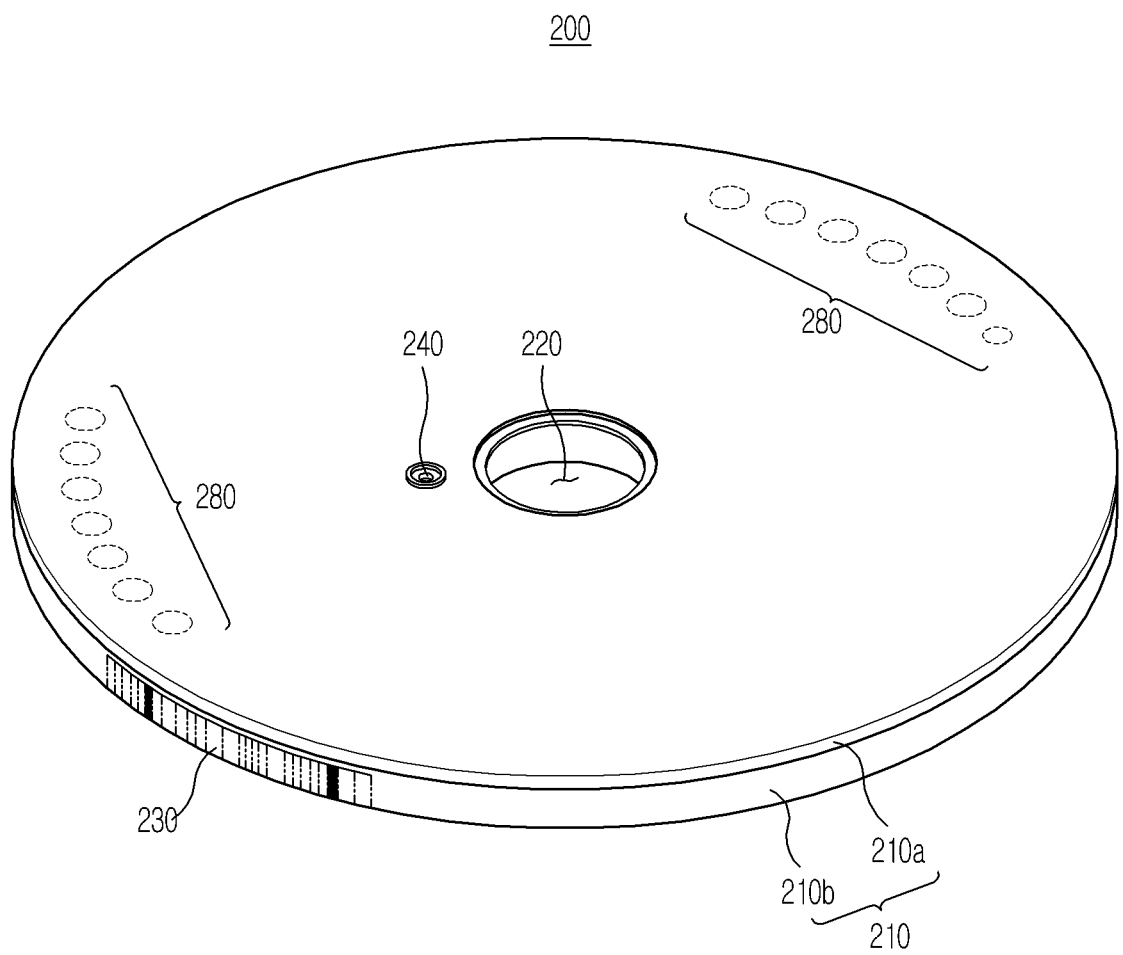
FIG. 9 is a perspective view illustrating a microfluidic device according to an exemplary embodiment.
Figure 10:
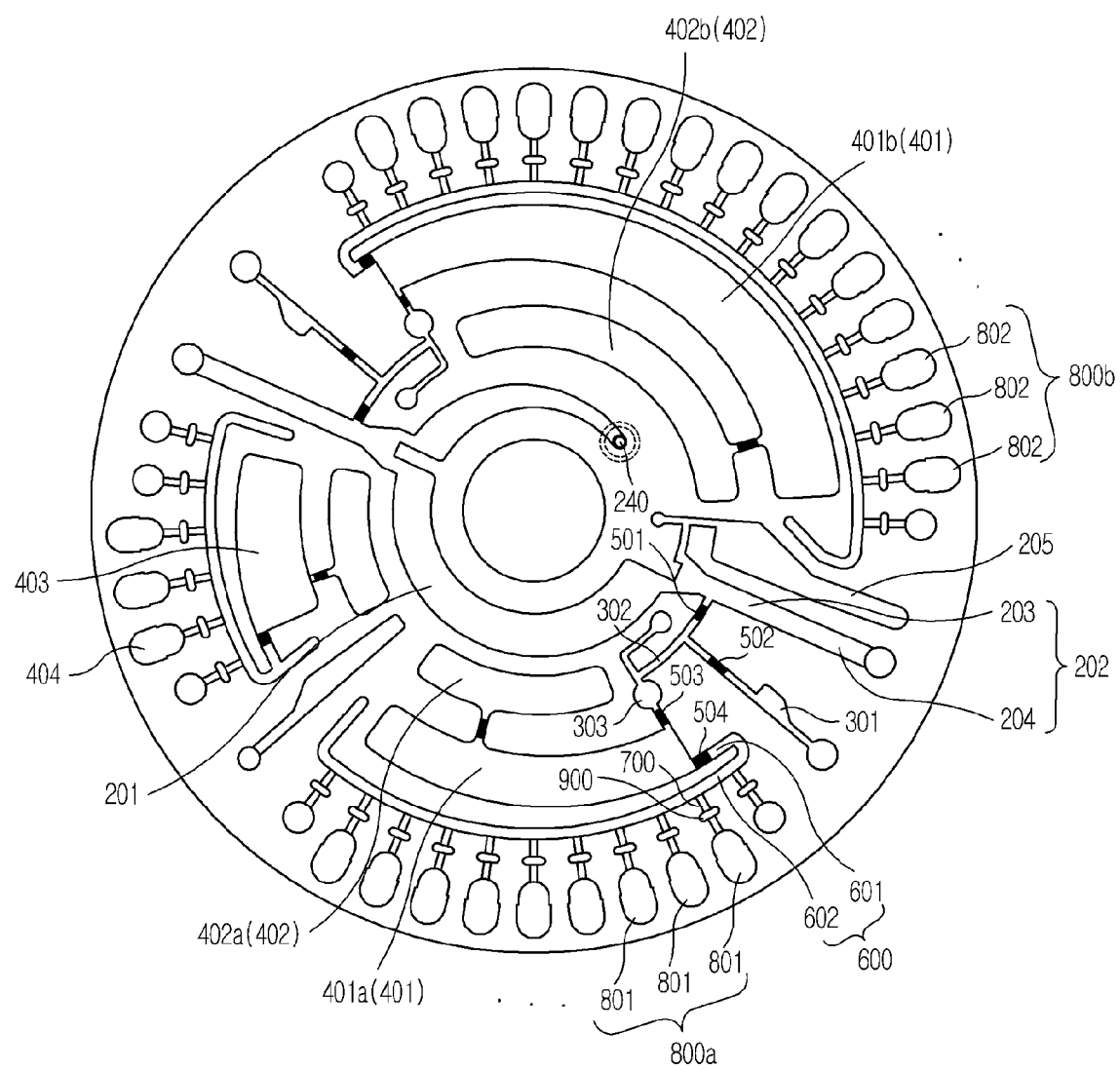
FIG. 10 is a plan view illustrating a configuration of the microfluidic device according to an exemplary embodiment.

FIG. 9 is a perspective view showing a microfluidic device according to an exemplary embodiment, while FIG. 10 is a plan view showing the microfluidic device according to the exemplary embodiment.

Referring to FIGS. 9 and 10, the microfluidic device 200 includes a rotatable disc-type platform 210, multiple chambers divided into compartments in the platform to contain a fluid (sample), multiple channels through which the fluid flows, and a bar code 230 provided on a lateral side of the platform 210.

The platform 210 may rotate about a center 220 thereof. In the multiple chambers and multiple channels placed inside the platform 210, the sample may be transferred, centrifuged and/or mixed using centrifugal force caused by rotation of the platform 210.

The platform 210 may be formed using biologically inactive acryl or other plastic materials including polydimethylsiloxane (PDMS), each of which is easily formable and has a biologically inactive surface. However, a raw material for formation of the platform 210 is not particularly limited and may include any materials with chemical or biological stability, optical transparency and/or mechanical workability.

The platform 210 may include multiple layers of plates. If a relief structure corresponding to a chamber or a channel is formed on facing sides of two of the plates, and if two or more relief structures are combined, an empty space and/or channel will be created inside the platform.

For instance, the platform 210 may include a first plate 210a and a second plate 210b attached with the first plate 210a, or may include a chamber positioned between the first plate 210a and second plate 210b, in which a fluid is contained. A compartment (not shown) may also be included to define a channel through which the fluid flows. Alternatively, the platform 210 may have different forms. The first plate 210a and the second plate 210b may be fabricated using thermoplastic resins.

Combination of the first plate 210a and the second plate 210b may be achieved by various techniques, such as the use of an adhesive or a pressure-sensitive adhesive tape, ultrasonic welding, laser welding, etc.

Hereinafter, a detailed description will be given of microfluidic structures assembled inside the platform 210 which are utilized for testing of a sample.

The sample may include a mixture of a fluid and a particulate material having a density higher than the fluid. For example, the sample may include a biological sample such as blood, saliva, urine, etc.

A sample chamber 201 may be placed on an inner part of the platform in a circumferential direction. The sample chamber 201 may be partitioned into compartments to contain a desired amount of sample. A sample inlet port 240 through which the sample is fed into the sample chamber 201 may be formed on a top of the sample chamber 201.

A sample separation chamber 202 may be placed on an outer part of the sample chamber 201 in a radial direction, in order to centrifuge the sample by rotation of the platform 210.

An excess sample-containing chamber 205 may be provided on one side of the sample separation chamber 202. If excess sample is introduced into the sample chamber 201, a desired amount of the sample for testing will remain in the sample chamber while the excess sample flows into the excess sample-containing chamber 205.

If the sample is blood, the application of centrifugal force will cause relatively heavy blood cells settle to the bottom of the sample separation chamber 202, while relatively light serum remains above the blood cells, thereby separating the serum from the blood cells.

The sample separation chamber 202 may include a channel-type supernatant collector segment 203 extending from the sample chamber 201 in a radial direction, and a precipitate collector segment 204 which is located at an end of the supernatant collector segment 203. The precipitate collector segment 204 forms a space to collect a precipitate with relatively high specific gravity, such as the blood cells, while the supernatant collector segment 203 collects a supernatant, such as the serum.

A guide channel 302 may be placed on one side of the sample separation chamber 202 to guide the separated supernatant from the sample separation chamber 202 to a dilution chamber 401, in which a diluent is contained.

Along the guide channel 302, a metering chamber 303 may be formed at an inlet of the dilution chamber 401 to temporarily store and measure the supernatant. A supernatant removal chamber 301 may also be provided in connection with the guide channel 302 to remove residual supernatant which remains in the guide channel 302 after the supernatant is received in the metering chamber 303.

At least one dilution chamber 401 is provided at an outlet of the metering chamber 303. More than one dilution chamber 401 may be provided such as a first dilution chamber 401a and a second dilution chamber 401b, and may contain different amounts of dilution buffer, respectively. According to a desired volume of the dilution buffer, the multiple dilution chambers 401a and 401b may have different volumes. Each dilution chamber 401 may be further partitioned into a second compartment 402, including a second compartment 402a of the first dilution chamber 401a and a second compartment 402b of the second dilution chamber 401b. The microfluidic device 200 according to an exemplary embodiment includes the first dilution chamber 401a and the second dilution chamber 401b containing different volumes of dilution buffer, respectively, so as to vary a dilution ratio.

The microfluidic device 200 may also include a control dilution chamber 403, which does not receive the sample from the sample separation chamber 202 and only stores the dilution buffer. The control dilution chamber 403 provides a reference value for reaction detection. At least one control chamber 404 may be provided outside the dilution chamber 403 without receiving the sample, in order to obtain a standard detection value (sometimes referred to as zero-point).

A distribution channel 600 is connected with the outlet of the dilution chamber 401. The distribution channel 600 has a first (front end) section 601 extending from the outlet of the dilution chamber 401 outside the platform 210, and a second (rear end) section 602 extending from an outmost end of the first section 601 in a circumferential direction. An end of the second section 602 may be connected to a venting hole (not shown). The venting hole (not shown) may preferably be positioned at a location at which the sample will not escape when distributing the sample from the dilution chamber 401 to the distribution channel 600 by centrifugal force. The distribution channel 600 exhibits a constant fluid resistance from the first front end section 601 connected with the outlet of the dilution chamber 401 to the second rear end section 602 connected with the exhaust pipe (not shown). That is, the constant fluid resistance is exhibited over the entirety of the distribution channel 600, including the first front end section 601 and the second rear end section 602. In order to maintain a constant fluid resistance, the distribution channel 600 may have a fixed cross section. As a result, resistance to fluid migration applied during distribution of the sample may be considerably eliminated, in turn rapidly and effectively distributing the sample from the dilution chamber 401.

A first reaction chamber group 800a and a second reaction chamber group 800b corresponding to the first and second dilution chambers 401a and 401b, respectively, are placed outside the first and second dilution chambers 401a and 401b. In particular, the first reaction chamber group 800a is positioned outside the first dilution chamber 401a. Likewise, the second reaction chamber group 800b is provided outside the second dilution chamber 401b.

Each of the reaction chamber groups 800a and 800b may have at least one reaction chamber 801 or 802, respectively, and such reaction chambers 801 and 802 are connected with the corresponding dilution chamber 401 through the distribution channel 600 to distribute a diluted sample. Each of the reaction chamber groups 800a and 800b may have only a single reaction chamber.

Each reaction chamber 801 or 802 may be a closed chamber. A closed chamber refers to a reaction chamber 801 or 802 without an exhaust vent. Multiple reaction chambers 801 and 802 may contain a variety of reagents with different concentrations introduced in advance, in order to allow an optically detectable reaction of the reagent with the diluted sample introduced through the distribution channel 600. The optically detectable reaction may include, for example, fluorescence, variation of optical density, and the like. However, use of the reaction chambers 801 and 802 is not particularly limited to the foregoing applications.

Multiple reaction chambers 801 and 802 in the corresponding reaction chamber groups 800a and 800b may contain desired reagents to be reacted with the diluted sample in a constant dilution ratio thereof.

For instance, the first reaction chamber group 800a may contain some reagents reacting with serum in a dilution ratio of 100:1 of diluent to serum in order to detect substances in the serum such as triglycerides (TRIG), total cholesterol (Chol), glucose (GLU), urea nitrogen (BUN), etc. The second reaction chamber group 800b may contain other reagents reacting with serum in a dilution ration of 20:1 of diluent to serum in order to detect substances in the serum such as direct bilirubin (DBIL), total bilirubin (TBIL), gamma glutamyl transferase (GGT), etc. Since multiple reaction chambers 802 in the second reaction chamber group 800b receive a diluted sample from the second dilution chamber 401b, wherein the diluted sample has a dilution ratio different from that of another diluted sample introduced into the first reaction chamber group 800a, it is preferable that the reaction chambers 801 and 802 in the corresponding reaction chamber groups 800a and 800b contain different reagents suitable for the diluted samples and their corresponding dilution ratios.

The reaction chambers 801 and 802 may have the same volume (or capacity), however, such volume or capacity is not particularly limited. If diluted samples and/or reagents having different volumes are required depending on the tests to be conducted, the reaction chambers 801 and 802 may have different volumes or capacities.

The multiple reaction chambers 801 and 802 may be chambers having vents and inlet ports (not shown).

These reaction chambers 801 and 802 may be connected with the second section 602 through inlet channels 700. Each of the inlet channels 700 may be fabricated to branch off of the distribution channel 600. Here, the inlet channel 700 may be connected with the distribution channel 600 at a right angle so as to form a "T" shape with the distribution channel. The inlet channel 700 extends in a radial direction of the platform 210.

Channels connecting separate chambers may have valves 501, 502, 503 and 504. The valves 501, 502, 503 and 504 may include: a first valve 501 placed about midway along the guide channel 302 to open and close the outlet of the sample separation chamber 202; a second valve 502 placed about midway along the supernatant removal chamber 301 to open and close the supernatant removal chamber 301; a third valve 503 placed between the metering chamber 303 and the dilution chamber 401 to open and close an outlet of the metering chamber 303; and a fourth valve 504 placed at the outlet of the dilution chamber 401 to open and close the distribution channel 600.

Each of these valves 501, 502, 503 and 504 may be, for example, a capillary valve passively opened when a constant pressure is applied thereto; a valve receiving power or energy supplied from an external source and actively running by actuation signal; or any one of other conventional valves. The microfluidic device 200 according to one exemplary embodiment adopts a phase transition valve driven by external energy.

The valves are aligned between an upper first plate 210a and a lower second plate 210b of the platform 210 in a planar form or three-dimensional form to block fluid flow. During actuation of the valves, the valve material is fused at a high temperature, and the valve material flows into a free space adjacent to the valve, in turn opening the corresponding channel which the valve previously blocked.

In order to heat and fuse the valves 501, 502, 503 and 504, an external energy source 122 for light emission (see FIG. 13) is movably mounted outside the platform 210, so that the energy source 122 can radiate light to a region of the valves 501, 502, 503 and 504.

Accordingly, the external energy source 122 moves over the top of any one of the valves 501, 502, 503 and 504 to be opened depending on progress of a testing process, and the light source 122 then radiates light downward to open the corresponding valve 501, 502, 503 and 504.

Each of the valves 501, 502, 503 and 504 may be fabricated using a phase transition material with heating particles dispersed in the phase transition material.

Each of the heating particles may have a size sufficient to freely migrate inside a channel having a width from several hundreds to several thousands of micrometers (μm). The heating particles are designed so as to rapidly increase in temperature through efficient absorption of light (for example, laser light) radiated thereto. For this purpose, the heating particle may have a core containing metal components and a hydrophobic shell. More particularly, the heating particle may have a structure with an iron (Fe) core and a shell including multiple surfactant components to be combined with Fe and cover the Fe core. The heating particle may be a material dispersed in a carrier oil, which is commercially available. The phase transition material may be wax. When the heating particle absorbs light energy and transfers the same in a heat energy status to the surrounding phase transition material such as wax, the wax is liquefied. As a result, the valve is collapsed to open a fluid path. The wax has a suitably high melting point. If the melting point is too high, it takes a long time to melt the wax by light radiation, thus causing difficulties in precise control of an open timing of the fluid path. On the other hand, if the melting point is too low, the wax is partially molten without light emission, thus causing problems of fluid leakage. Such wax may include, for example, paraffin wax, microcrystalline wax, synthetic wax, natural wax, and the like.

The phase transition material may be a gel or thermoplastic resin. Such a gel may be prepared using polyacrylamide, polyacrylate, polymethacrylate, polyvinylamide, and so forth. The thermoplastic resin may include, for example, COC, PMMA, PC, PS, POM, PFA, PVC, PP, PET, PEEK, PA, PSU, PVDF, etc.

A bar code 230 may be formed on a lateral side of the platform 210, as shown in FIG. 9. The bar code 230 may contain a variety of information, such as production date, expiration date, etc.

The bar code 230 may be a one-dimensional (1D) bar code; however, in order to store a large amount of information in the bar code, various types of bar codes including a two-dimensional (2D) bar code such as a matrix code may be used.

Alternatively, the bar code 230 may also be replaced by a hologram, RFID tag or memory chip to store information therein. When a storage medium to read and write information therein is used, such as a memory chip, a wide range of information such as sample test results, patient information, blood sampling date and time, test execution date and time, information as to whether a test was executed, identification information, etc. may be stored in the memory chip.

Since the multiple reaction chambers 801 and 802 are aligned next to each other, cross-contamination may occur when contents of one of the chambers 801 in reaction chamber group 800a flows into another chamber 801 in reaction chamber group 800a. Fluid contained in one of the chambers 802 in the second reaction chamber group 800b may flow into another chamber 802 in the second reaction chamber group 800b. Due to this potential for cross-contamination, it is difficult to obtain accurate sample test results.

Therefore, the microfluidic device 200 further includes a delay structure 900 to reduce cross-contamination between the reaction chambers of the same reaction chamber group.

Figure 11:
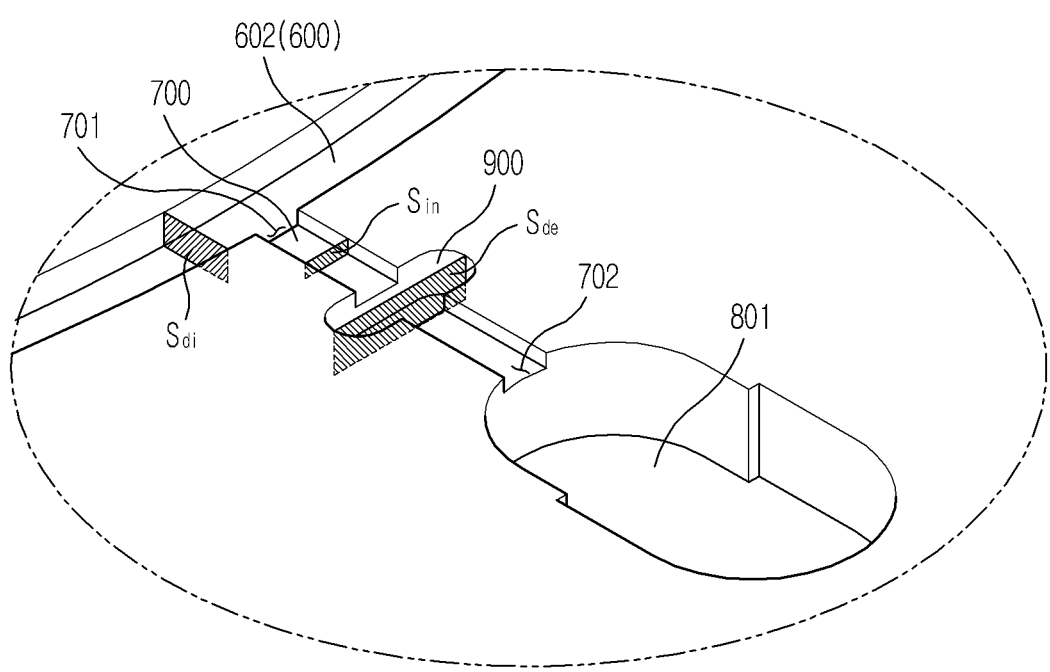
FIG. 11 is an enlarged perspective view illustrating a reaction chamber unit of the microfluidic device according to an exemplary embodiment.
Figure 12:
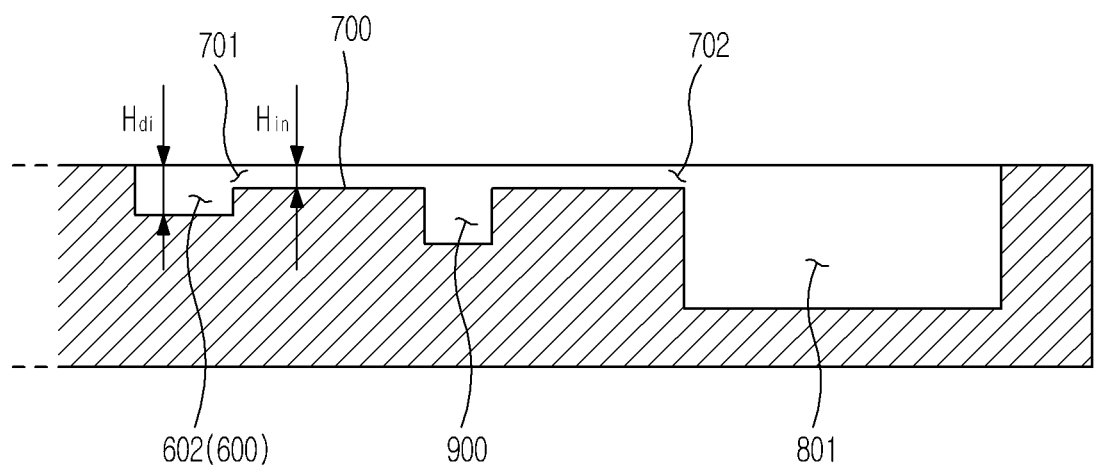
FIG. 12 is an enlarged cross-sectional view illustrating a reaction chamber unit of the microfluidic device according to an exemplary embodiment.

FIG. 11 is an enlarged perspective view illustrating a reaction chamber 801, inlet channel 700 and delay structure 900 of a microfluidic device 200 according to one exemplary embodiment. FIG. 12 is an enlarged cross-sectional view illustrating the same.

Referring to FIGS. 11 and 12, the microfluidic device 200 includes the distribution channel 600, the inlet channel 700, the reaction chamber 801, and the delay structure 900 placed between the second section 602 of the distribution channel and the reaction chamber 801. The inlet channel 700 has an inlet 701 and an outlet 702, wherein the inlet 701 is connected with the second section 602, and wherein the outlet 702 is connected with the reaction chamber 801.

The reaction chamber 801 may contain a reagent or a reaction product of a sample and the reagent. The contents of the reaction chamber 801 may exit the reaction chamber 801 by diffusion or turbulent flow generated in the reaction chamber 801.

The delay structure 900 is provided to delay transfer of the contents of the reaction chamber 801 toward the second section 602. A material exiting the reaction chamber 801 passes through the delay structure 900 before flowing into the second section 602. Accordingly, the delay structure 900 may delay flow of a fluid or material exiting any one reaction chamber 801 into another chamber 801 adjacent to the former chamber.

The delay structure 900 may be formed on the inlet channel 700. The delay structure 900 may be a chamber having an inlet and an outlet which are connected with the inlet channel 700.

In order to reduce a diffusion velocity of a material in the delay structure 900, a cross-sectional area (Sde) of the delay structure in which the fluid flows may be substantially larger than a cross-sectional area (Sin) of the inlet channel 700. In an exemplary embodiment, the cross-sectional area Sde may be double the cross-sectional area Sin in order to effectively delay the fluid flow or the diffusion of the material since the fluid or material will fill the large chamber in the delay structure before continuing through the inlet channel 700 to the second section 602.

As the cross-sectional area of the inlet channel 700 is decreased, resistance to the fluid passing through the inlet channel 700 may be increased. Accordingly, in order to extend a time required for the fluid of the reaction chamber 801 to pass through the inlet channel 700 and flow into the second section 602, the cross-sectional area Sin of the inlet channel 700 is at least smaller than a cross-sectional area (Sdi) of the second section 602. In this case, the resistance to the fluid flowing through the inlet channel 700 may be equal to or higher than a resistance to the fluid flowing through the second section 602.

When a material exiting any one reaction chamber 801 flows into the second section 602, it is necessary to prevent the material from flowing into the other chamber 801 adjacent to the former chamber. For this purpose, a bottom surface of the second section 602 may be located below a bottom surface of the inlet channel 700. That is, if a top surface of the second section 602 is the same as a top surface of the inlet channel 700, a height (Hdi) of the second section 602 is duly higher than a height (Hin) of the inlet channel 700. If the second section 602 is connected with the inlet channel 700 by a stepped interval in order to allow the bottom surface of the second section 602 to be positioned below a bottom surface of the inlet channel 700, a fluid present at a level lower than the bottom surface of the inlet channel 700 cannot flow into the inlet channel 700.

Most of the sample fed into the second section 602 by centrifugal force flows toward the reaction chamber 801 along the inlet channel 700 at a location at which the second section 602 is connected with the inlet channel 700. While the sample flows into the delay structure 900, air contained in the reaction chamber 801 may be exhausted into the second chamber 602. When filling one of the reaction chambers 801 with the sample, the sample does not further flow into the same reaction chamber 801; instead, the sample is moved along the second section 602 to fill the other chambers 801 adjacent to the former chamber 801. However, even if one reaction chamber 801 is not fully filled, the sample may partially flow toward the other chamber 801 adjacent to the former chamber.

The sample flowing into the reaction chamber 801 may react with a reagent contained in the reaction chamber 801. The reagent or a reaction product may flow or pass back through the inlet channel 700 by diffusion, thus flowing into the second section 602. A reagent or reaction product exiting the reaction chamber 801 firstly passes through the delay structure 900. Then, after passing through the delay structure 900, the reagent or the reaction product flowing toward the second section 602 cannot easily flow into the inlet channel 700 between the delay structure 900 and section 602, owing to a difference in height between the bottom surface of the second section 602 and the bottom surface of the inlet channel 700. Finally, even if the reagent or the reaction product flows into the inlet channel 700 of an adjacent reaction chamber 801, this reagent or reaction product must pass the delay structure 900 in the adjacent inlet channel 700, in turn delaying flow of the reagent or the reaction product into the adjacent reaction chamber 801.

Figure 13:
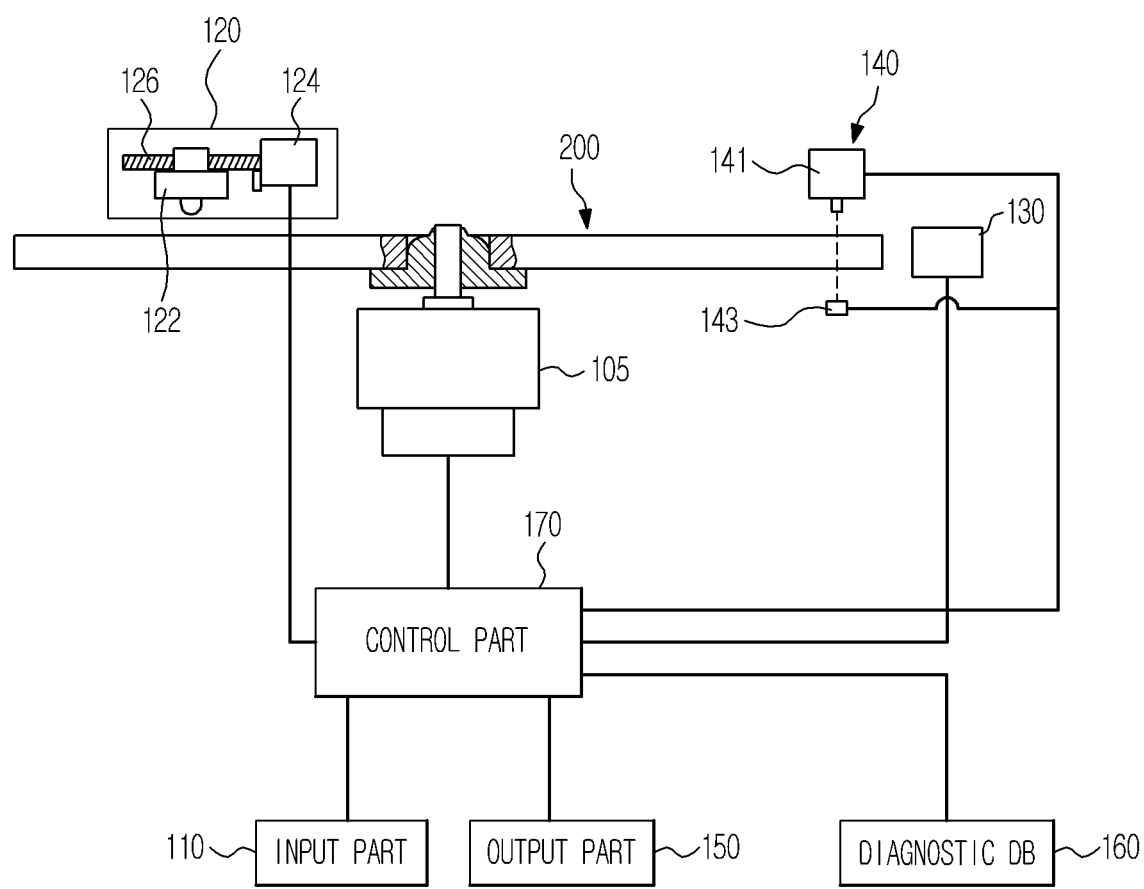
FIG. 13 is a view illustrating a sample testing apparatus including the microfluidic device according to an exemplary embodiment.

FIG. 13 shows a configuration of a sample testing apparatus including a microfluidic device according to an exemplary embodiment. The sample testing apparatus includes a spindle motor 105 to rotate the microfluidic device 200, a data reader 130, a valve opening device 120, an inspection unit 140, an input unit 110, an output unit 150, a diagnostic database (DB) 160, and a control unit 170 controlling individual devices described above.

The spindle motor 105 rotates the microfluidic device 200, and stops and rotates the same in order to move the device to a desired position.

Although not shown in the drawing, the spindle motor 105 may further include a motor driving device for controlling an angular position of the microfluidic device. For example, the motor driving device may use a stepper motor or a DC motor.

The data reader 130 may be, for example, a bar code reader. Such a data reader 130 reads data stored in the bar code 230 and transfers the read data to the control unit 170. The control unit 170 actuates individual devices based on the read data, thus driving the sample testing apparatus.

The valve opening device 120 is provided to open and close at least one valve 501, 502, 503 or 504 of the microfluidic device 200, and includes an external energy source 122 and a movement unit 124 and 126 to move the external energy source 122 to a location of a valve to be opened.

The external energy source 122 may emit electromagnetic radiation, and may include, for example, a laser source to radiate a laser beam, a light emitting diode to radiate visible or infrared light, a xenon lamp, etc. In particular, the laser source may have at least one laser diode.

The movement unit 124 and 126, provided to adjust a position of the external energy source 122 so as to concentrically radiate the energy to the valve, may include a driving motor 124 and a gear unit 126 configured with the external energy source 122 to move the same by rotation of the driving motor 124. The movement unit 124 and 126 may be embodied according to a variety of mechanisms.

The inspection unit 140 may include at least one light emission unit 141 and at least one light receiving unit 143 which corresponds to the light emission unit 141 and receives light penetrating a reaction chamber 801 of the microfluidic device 200.

The light emission unit 141 may be a light source flashing at a specific wavelength, which includes, for example, a semiconductor light emitting device such as a light emitting diode or a laser diode, a gas discharge lamp such as a halogen lamp or a xenon lamp, etc.

The light emission unit 141 is placed over a site of the microfluidic device 200 at which light emitted from the light emission unit 141 passes through the reaction chamber 801 and reaches the light receiving unit 143.

The light receiving unit 143 generates electrical signals according to an intensity of incident light and employs, for example, a depletion layer photodiode, a avalanche photodiode, a photomultiplier tube, etc.

The control unit 170 controls the spindle motor 105, the data reader 130, the valve opening device 120 and/or the inspection unit 140 in order to smoothly operate the sample testing apparatus. The control unit 170 also searches the diagnostic database 160 and compares information detected from the inspection unit 140 with information in the diagnostic database 160, so as to make a disease diagnosis based upon analysis of blood contained in the reaction chamber 801 of the microfluidic device 200.

The input unit 110 is provided to input detectable test items based on types of the sample fed and/or introduced into the microfluidic device 200, and may be a touch screen type input device mounted on the sample testing apparatus.

The output unit 150 outputs diagnostic results and information as to whether diagnosis is completed or not, and may include a visible output device such a liquid crystal display, an audio output device such as a speaker, or an audiovisual output device.

Although a few exemplary embodiments have been shown and described, it will be appreciated by those skilled in the art that changes may be made in these embodiments without departing from the principles and spirit of the inventive concept, the scope of which is defined in the claims and their equivalents.

What is claimed is:

1. A microfluidic device comprising:
   at least one reaction chamber which contains a reagent capable of reacting with a sample;
   a distribution channel through which the sample is provided to the at least one reaction chamber;
   an inlet channel through which the at least one reaction chamber is connected with the distribution channel; and
   a delay structure which is located between the at least one reaction chamber and the distribution channel, and delays movement of contents of the reaction chamber to the distribution channel, the delay structure comprising a chamber that includes an inlet and an outlet which are respectively connected with the inlet channel,
   wherein a cross-sectional area of the delay structure through which the sample flows is larger than a cross-sectional area of the inlet channel,
   wherein the cross-sectional area of the inlet channel is smaller than a cross-sectional area of the distribution channel, and
   wherein a bottom surface of the distribution channel is positioned at a level lower than a bottom surface of the inlet channel, a bottom surface of the delay structure is positioned at a level lower than the bottom surface of the distribution channel, and a bottom surface of the reaction chamber is positioned at a level lower than the bottom surface of the delay structure.

2. The microfluidic device according to claim 1, wherein the contents are the reagent contained in the reaction chamber or a reaction product of the reagent combined with the sample.

3. The microfluidic device according to claim 1, wherein the delay structure is provided at the inlet channel.

4. The microfluidic device according to claim 1, wherein a cross-sectional area of the delay structure through which the sample flows is at least twice a cross-sectional area of the inlet channel.

5. The microfluidic device according to claim 1, wherein the inlet channel is branched from the distribution channel.

6. The microfluidic device according to claim 1, wherein the inlet channel and the distribution channel have structures so that a resistance to the sample when the sample flows into the inlet channel from the reaction chamber is equal to or higher than a resistance to the sample when the fluid sample flows through the distribution channel.

7. The microfluidic device according to claim 1, further comprising a valve provided at the inlet of the distribution channel.

8. The microfluidic device according to claim 7, wherein the valve is a phase transition valve actuated in a non-contact manner by an external energy source.

9. The microfluidic device according to claim 1, wherein the sample is a fluid.

10. A microfluidic device comprising:
    a sample chamber which contains a sample;
    a distribution channel which is connected with the sample chamber and through which the sample flows;
    a plurality of reaction chambers which contain at least one reagent that is capable of reacting with the sample;
    a plurality of inlet channels through which the distribution channel is connected with the reaction chambers; and
    a plurality of delay structures which are located between the reaction chambers and the distribution channel and delay flow of contents of the reaction chambers to the distribution channel, each of the delay structures comprising a chamber that includes an inlet and an outlet which are respectively connected with the inlet channel, and
    wherein a bottom surface of the distribution channel is positioned at a level lower than a bottom surface of each inlet channel of the plurality of inlet channels, wherein a bottom surface of each of the plurality of delay structures is positioned at a level lower than the bottom surface of the distribution channel, and a bottom surface of each of the reaction chambers is positioned at a level lower than the bottom surface of each of the plurality of delay structures.

11. The microfluidic device according to claim 10, wherein each of the plurality of delay structures is located between a corresponding reaction chamber of the plurality of reaction chambers and the distribution channel.

12. The microfluidic device according to claim 10, wherein each of the plurality of delay structures is formed in a corresponding inlet channel of the plurality of inlet channels.

13. The microfluidic device according to claim 10, wherein a cross-sectional area of each of the delay structures through which the sample flows is at least twice a cross-sectional area of each inlet channel of the plurality of inlet channels.

14. The microfluidic device according to claim 10, wherein a cross-sectional area of the distribution channel is constant over the entirety of the distribution channel.

15. A centrifugal microfluidic device comprising:
a rotational platform comprising:
a reaction chamber which contains a reagent capable of reacting with a sample;
a distribution channel through which the sample is provided to the reaction chamber;
an inlet channel which connects the reaction chamber with the distribution channel; and
a delay structure which is located between the reaction chamber and the distribution channel and delays movement of contents of the reaction chamber to the distribution channel, the delay structure comprising a chamber that includes an inlet and an outlet which are respectively connected with the inlet channel,
wherein the distribution channel has a first section extending outward in a radial direction of the platform and a second section extending from the first section in a circumferential direction of the platform,
wherein a bottom surface of the second section is positioned at a level lower than a bottom surface of the inlet channel, so that the inlet channel is connected with the second section by a stepped interval, and
wherein a bottom surface of the second section of the delay structure is positioned at a level lower than the bottom surface of the distribution channel, and a bottom surface of the reaction chamber is positioned at a level lower than the bottom surface of the delay structure.

16. The centrifugal microfluidic device according to claim 15, further comprising a sample chamber, wherein the distribution channel is connected with an outlet of the sample chamber.

17. A centrifugal microfluidic system comprising:
a microfluidic device; and
a rotational driving device which supports and rotates the microfluidic device, wherein the microfluidic device comprises: a plurality of chambers which contains a fluid;
at least one channel through which the plurality of chambers are interconnected and through which the fluid flows;
at least one valve which opens or closes the at least one channel; a reaction chamber which contains a reagent capable of reacting with a sample; an inlet channel having an inlet through which the fluid is provided from the at least one channel and an outlet through which the fluid is provided from the inlet channel into the at least one reaction chamber; and
a delay chamber located between the inlet and the outlet of the inlet channel to delay movement of contents of the reaction chamber toward the inlet, the delay chamber comprising a an inlet and an outlet which are respectively connected with the inlet channel, and
wherein a bottom surface of the at least one channel through which the fluid is provided to the inlet channel is positioned at a level lower than a bottom surface of the inlet channel, and wherein a bottom surface of the delay chamber is positioned at a level lower than the bottom surface of the at least one channel through which the fluid is provided to the inlet channel, and a bottom surface of the reaction chamber is positioned at a level lower than the bottom surface of the delay chamber.

18. The centrifugal microfluidic system according to claim 17, further comprising an optical detection unit which optically detects a reaction result in the reaction chamber.

19. The centrifugal microfluidic system according to claim 17, further comprising a valve driving unit which opens the valve.

* * * * *